United States Patent [19]

Conkle et al.

[11] 4,170,901
[45] Oct. 16, 1979

[54] SORPTION TUBE ATMOSPHERIC SAMPLING SYSTEM

[75] Inventors: James P. Conkle; William W. Lackey, both of San Antonio; Charles L. Martin, Lytle, all of Tex.

[73] Assignee: The United States of America as represented by the Secretary of the Air Force, Washington, D.C.

[21] Appl. No.: 915,710

[22] Filed: Jun. 15, 1978

[51] Int. Cl.$^2$ .................. G01N 1/24; G01N 15/00
[52] U.S. Cl. .................. 73/421.5 R; 219/535
[58] Field of Search .................. 73/421.5 R; 285/DIG. 18; 23/232 R; 219/535

[56] References Cited

U.S. PATENT DOCUMENTS

| | | | |
|---|---|---|---|
| 1,834,581 | 12/1931 | Farrell et al | 285/Dig 18 |
| 3,095,739 | 7/1963 | Doolittle | 73/421.5R |
| 3,521,493 | 7/1970 | Guizouarn et al | 73/421.5R |
| 3,748,905 | 7/1973 | Fletcher et al | 73/421.5R |
| 3,932,807 | 1/1976 | Wilson | 73/23X |
| 4,046,014 | 9/1977 | Boehinger et al | 73/21.5R |
| 4,091,674 | 5/1978 | Amery | 73/421.5R |

Primary Examiner—Daniel M. Yasich
Attorney, Agent or Firm—Joseph E. Rusz and Jacob N. Erlich

[57] ABSTRACT

A sorption tube atmospheric sampling system having a sorption tube, a vacuum pump and a flow meter. The sorption tube is made of a hollow elongated tubular-shaped element of rigid, non-corrosive material having a pair of mesh filters located at each end thereof and the sorbent material located therebetween. After the sampling operation has been completed, analysis of the collected pollutants within the sorption tube is accomplished by means of a conventional gas chromatography-mass spectrometry analysis in which Helium is passed through the sorption tube while the tube is located within a uniquely designed thermal desorption block. The desorption block is configured so as to encompass the sorption tube during utilization thereof. As a result, it is now possible to utilize the same sorption tube for both the sampling and desorption operation.

5 Claims, 3 Drawing Figures

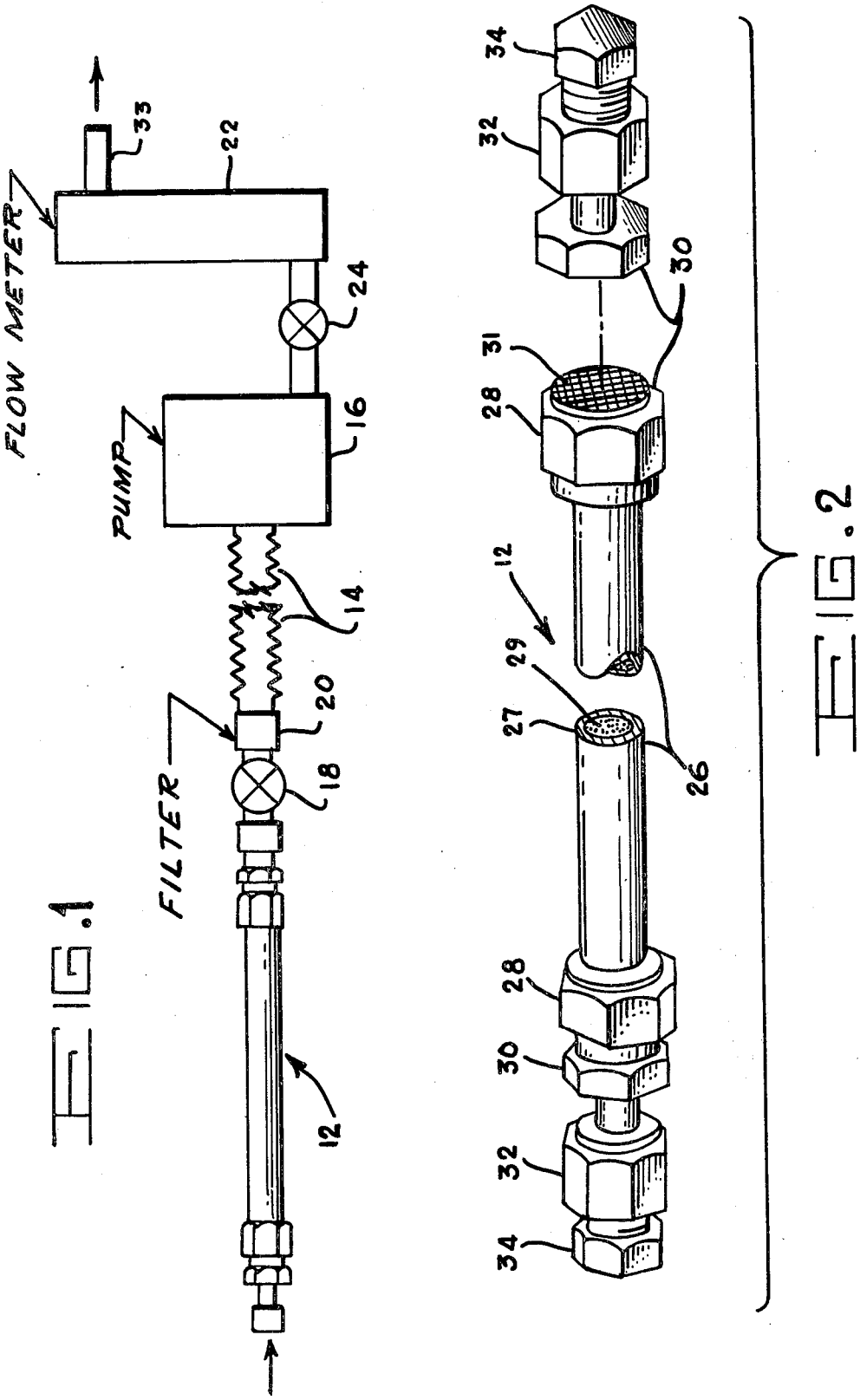

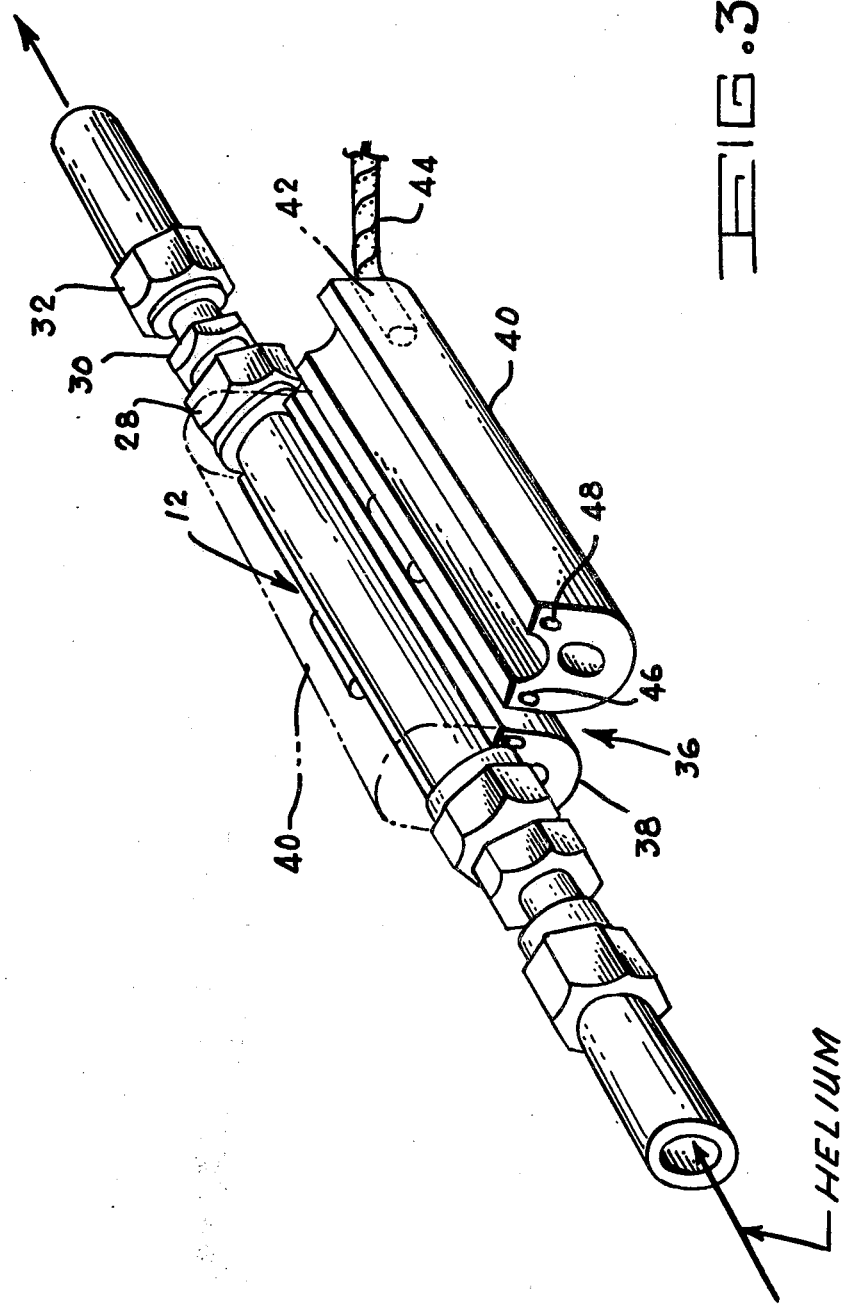

SORPTION TUBE ATMOSPHERIC SAMPLING SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates generally to an atmospheric sampling system, and, more particularly to a sorption tube atmospheric sampling system which incorporates therein a uniquely designed sorption tube, a pump and flow meter as well as a thermal desorption block for use during sample analysis.

An ever expanding field of study is the study and research of pollutants in the air. It is essential to continuously sample the atmosphere for the following reasons:
1. compliance with OSHA health standards;
2. compliance with EPA standards;
3. as a guide in industrial air pollution;
4. to assess atmospheric quality;
5. to study jet engine combustion products;
6. to analyze and study gasoline combustion products;
7. to study and analyze diesel engine combustion products;
8. to determine chemical contamination of water and food;
9. to study the closed environment; and
10. to evaluate the atmosphere in bio-medical experimentation.

Atmospheric sampling systems in the past have generally comprised of a cryogenic trapping system which requires considerable equipment in field operations and extensive sampling intervals for proper analysis of the atmosphere. To overcome these deficiencies the sorbent tube atmospheric sampling system was developed. Examples of such a sampling system can be found on pages 552–555 and pages 556–560 in the June 1975, Volume 9, No. 6 issue of Environment Science and Technology as well as pages 1118–1191, Volume 47, No. 7 of the June 1975 issue of Analytical Chemistry. Although sorption tube sampling systems have proved to be more desirable than the cryogenic sampling systems of the past the need still exists for a rugged sampling system which is not only portable but also capable of withstanding the rigors of field use and freight shipment without subsequent damage and therefore degeneration of the sampled materials. In addition, it would be desirable to provide a sorption tube in which the sample collected would not have to be removed prior to desorption. Furthermore, it would be substantially more economical if the same sorption tube was capable of trapping the atmospheric pollutants as well as providing a container for use during the desorption operation.

SUMMARY OF THE INVENTION

The instant invention overcomes the problems encountered in the past by providing a compact sorbtion tube atmospheric sampling system which is capable of reliably removing the contaminants or pollutants from the atmosphere. This is accompliahed by means of lightweight, rugged sorbtion tube which can be subsequently utilized in conjunction with a thermal desorption block in a conventional gas chromatography-mass spectrometry analysis arrangement.

The compact sorption tube atmospheric sampling system of this invention is made up of the following basic elements. A sorption tube, a pump, and a flow meter. In addition, the sorption tube is utilized in conjunction with a uniquely designed thermal desorption block in a conventional analysis system.

The sorption tube is an elongated hollow tube made of stainless steel having a pair of end couplings, each coupling containing therein a stainless steel screen. Located within the tube and contained between the two stainless steel screens is any suitable sorbent material such as 35–60 mesh Tenax. In addition each coupling of the sorption tube is attached to a conventional vacuum coupling for use within the sampling system set forth above as well as the desorption block of the analysis system. A special plug and Teflon washer are utilized to seal each end of the sorbtion tube when the tube is disconnected from the sampling system or the desorption system and in transit or storage.

During the atmospheric sampling operation, the sorption tube is formed as a part of the sampling system of this invention and, more specifically is operably connected to a ball valve, a filter, a vacuum pump, a needle valve and a flow meter. During actual atmospheric sampling, the sorbtion tube is placed in the environment to be sampled and an airstream containing the contaminants or pollutants to be sampled is drawn through the stainless steel sorption tube by means of the vacuum pump. The ball valve starts and stops the operation of the system while the filter removes any dust particles which may have passed through the sorption tube and prevents them from entering the vacuum pump. Airflow is regulated by means of the flow meter and needle valve. Generally, a sample flow rate of one liter per minute is required during sampling operation. Upon completion of the sampling operation the ends of the sorption tube are sealed by means of the plug.

After sampling, the contaminents are removed by thermal desorption by a conventional gas chromatography-mass spectrometry operation. During this operation the sorption tube is placed within the thermal desorption block of this invention. The thermal desorption block is in the form of an aluminum clam-like structure formed of a pair of semi-circular housings which are fitted about the sorption tube. The thermal desorption block has two heaters therein as well as a platinum resistance thermal controller and a thermocouple to monitor the block temperature. During the desorption operation the sealed ends of the sorption tube are opened by removal of the plug and helium is passed through the sorption tube while the sorption tube is in place within the thermal desorbtion block. Actual analysis and removal of the pollutants from the sorbtion tube are performed in a conventional manner.

It is therefore an object of this invention to provide a sorption tube atmospheric sampling system which is extremely compact in construction and capable of portable use in a wide variety of locations.

It is another object of this invention to provide a sorption tube atmospheric sampling system which utilizes therein a uniquely designed sorption tube.

It is still another object of this invention to provide a sorption tube atmospheric sampling system in which the sorption tube thereof can be utilized in conjunction with a specifically designed thermal desorption block in an analysis of the contaminants or pollutants within the atmosphere.

It is still a further object of this invention to provide a sorption tube atmospheric sampling system which is economical to produce and which utilizes conventional, currently available components that lend themselves to standard mass producing manufacturing techniques.

For a better understanding of the present invention, together with other and further objects thereof, reference is made to the following description taken in conjunction with the accompanying drawing and its scope will be pointed out in the appended claims.

DETAILED DESCRIPTION OF THE DRAWINGS

FIG. 1 is a schematic representation of the sorption tube atmospheric sampling system of this invention;

FIG. 2 is a pictorial representation of the sorption tube of the atmospheric sampling system of this invention shown partly in exploded and segmented fashion; and FIG. 3 is a pictorial representation of the sorption tube of this invention shown in position within the thermal desorption block of this invention.

DETAILED DESCRIPTION OF THE PREFERRED EMBODIMENT

Reference is now made to FIG. 1 of the drawing which shows in schematic fashion the compact sorption tube atmospheric sampling system 10 of this invention. Atmospheric sampling system 10 incorporates therein a sorption tube 12 to be described in detailed hereinbelow operably connected by means of a flexible hose 14 to any conventional vacuum or circulating pump 16 such as model MB-155 manufactured by the Metals Bellows Corporation of Sharon, MA. Located intermediate sorption tube 12 and line 14 is a conventional ball valve 18 as well as a very fine filter 20 such as a seven micron filter. Vacuum or circulating pump 16 is operably attached to any conventional flow meter 22 such as a Fisher and Porter 10A3665S flow meter. A conventional needle valve 24 is located between pump 16 and flow meter 22 in order to control the flow of air through sorption tube 12.

The detailed description of sorption tube 12 is set forth with respect to FIG. 2 of the drawing. Sorption tube 12 is made up of an elongated cylindrically-shaped tubular element 26 made of any suitable non-breakable, non-corrosive material such as stainless steel (316). It is preferable, although not limited thereto, that the tubular element 26 be approximately 1.27 cm by 15.24 cm, having a wall thickness of 0.89 mm. The interior wall 27 of stainless steel tubular element 26 is electro-polished to reduce the surface effects of the metal. Situated at each end of the tubular element 26 is a fitting 28 into which is removably mounted a coupling 30. Each coupling 30 contains therein a stainless steel screen 31. Located within tubular element 26 and contained between the pair of screens 31 is any suitable sorbent material 29 such as approximately 2.5 g of 35–60 mesh Tenax-GC (a porous polymer of 2, 4-diphenyl-p-phenylene oxide). Connected to each coupling 30 is vacuum coupling 32 which is utilized for attachment of one end of sorption tube 12 to the ball valve 18 of sampling system 10 of this invention or to any conventional desorption system (not shown). A specifically designed nylon plug 34 and a ⅛ inch thick (31.75 mm) Teflon washer (not shown) seal each end of tube 12 when the tube is disconnected from either the sampling or desorption system.

Sample collection by the sorption tube atmospheric sampling system 10 of this invention is accomplished by the connection of sorption tube 12 to pump 16 and flow meter 22 of sampling system 10 in the manner shown in FIG. 1 of the drawing. The air to be tested is brought into sorption tube 12 by means of an airstream drawn into and passed through tube 12 by pump 16. Ball valve 18 is utilized for the on/off operation of this invention.

An airstream, after passing through the sorbent material 29 located within sorption tube 12 then passes through filter 20 so as to remove any dust particles which may contaminate and prevent the proper operation of vacuum pump 16. Flow control of the system is accomplished by means of needle valve 24 while the flow rate is measured by means of flow meter 22. After passing through system 10 the airstream is vented to the atmosphere by means of outlet 33. For proper operation of the sampling system of this invention a one liter per minute flow rate is maintained throughout the system. After completion of the sampling operation, sorption tube 12 is sealed by means of plug 34 and can therefore be transported without worry of breakage or further contamination.

Analysis of the pollutants within the sorption tube 12 is accomplished by means of a conventional gas chromatography-mass spectrometry analysis and takes place by passing Helium through the sorption tube 12 while the sorption tube 12 is located within thermal desorption block 36 shown in FIG. 3 of the drawing.

Thermal desorption block 36 is made up of a clamshell type configuration having a lower semi-cylindrically-shaped housing 38 and an upper semi-cylindrically-shaped housing 40 which in its operable position encloses sorption tube 12 as shown in Phantom in FIG. 3 of the drawing. A plurality of heaters 42 are located within either half or both halves of the desorption block 36. Heaters 42 may be in the form of 300-watt heaters connected by any suitable electrical lead wire 44 to a power source (not shown). A platinum resistance thermal controller 46 and a thermo-couple 48 are utilized to monitor and regulate the temperature of block 36. Block 36 is generally constructed of any light weight conductive material such as aluminum and is designed with a minimum of mass to enhance the rapid heating and cooling of sorption tube 12.

As a result of the arrangement shown in FIGS. 1 and 3 of the drawing, it is now possible to utilize the same sorption tube 12 (shown in FIG. 2 of the drawing) for both the sampling and desorbtion operation without subjecting the contaminants or pollutants within tube 12 to further contamination. In addition, the utilization of stainless steel tube 12 substantially reduces the possible breakage of the tube.

Furthermore, due to its portable nature, sampling system 10 can be readily used during operation in the field. In addition, the rugged construction of the sorption tube 12 allow the instant invention to withstand field use as well as freight shipment. The design of thermal block 36 of this invention allows the sorption tube 12 to be removed at any time after desorption of a sample so that preparation may be made to run the next sample while a run is in progress. Stainless steel screens are utilized within sorption tube 12 so as to eliminate any contamination of the screen by the sorbent material 29. Furthermore, the small size of the sorption tube system 10 provides an advantage over currently used cryogenic trapping systems. The advantages being (1) less equipment is required in field operation, (2) shorter sampling time is required, and (3) analysis in time is reduced be approximately 1/6.

Although this invention has been described with reference to particular embodiments, it will be understood to those skilled in the art that this invention is also capable of further and other embodiments within the spirit and scope of the appended claims.

We claim:

1. A sorption tube atmospheric sampling system comprising a removable sorption tube, means operably connected to said sorption tube for drawing a preselected amount of air through said sorption tube in order to trap within said sorption tube contaminants in the atmosphere, means operably connected to said drawing means for regulating the amount of air drawn through said sorption tube, means operably connected to said regulating means for monitoring the amount of air drawn through said sorption tube, and a thermal desorption block for use with said sorption tube during removal and testing of said contaminants contained within said sorption tube, said sorption tube being in the form of a hollow, elongated element having a preselected tubular configuration made of a rigid, substantially non-corrosive material, said preselected tubular configuration conforming to the interior configuration of said thermal desorption block, said hollow, tubular-shaped element having a high polished interior surface, a fitting being attached to each end of said element, a coupling being removably mounted within each of said fittings, each of said couplings containing therein a stainless steel screen, a sorbent material being located within said hollow, tubular-shaped element between said screens for trapping therein said contaminants found in the atmosphere, a vacuum coupling being connected to at least one of said couplings containing a screen therein, said vacuum coupling being removably securable to said means for drawing a preselected amount of said air through said sorption tube during said contaminant trapping procedure and to a spectrometry analysis apparatus when said sorption tube is in position within said thermal desorption block during said contaminant removal and testing procedure.

2. A sorption tube atmospheric sampling system as defined in claim 1 wherein said elongated tubular-shaped element is made of stainless steel.

3. A sorption tube atmospheric sampling system as defined in claim 2 wherein said sorbent material is a porous polymer of 2,4 diphenyl-p-phenylene oxide.

4. A sorption tube atmospheric sampling system as defined in claim 1 wherein said thermal desorption block comprises a pair of semi-cylindrically-shaped housings pivotally connected together, each of said housings having a recessed portion therein, said recessed portions being matingly configurated to said preselected tubular configuration of said sorption tube and encompassing said sorption tube, a plurality of heaters located within at least one of said semi-cylindrically-shaped housings, a thermal controller located within at least one of said housings, and a thermocouple located within at least one of said housings, whereby in its operative position said thermal desorption block has its semi-cylindrically-shaped housings encompassing said sorption tube.

5. A sorption tube atmospheric sampling system as definded in claim 4 wherein said housings are made of aluminum.

* * * * *